United States Patent [19]
Masuda et al.

[11] Patent Number: 4,751,320
[45] Date of Patent: Jun. 14, 1988

[54] PHOSPHORIC ESTER AND PROCESS FOR PRODUCING SAME

[75] Inventors: Mitsuharu Masuda, Funabashi; Tomihiro Kurosaki, Ohsaka, both of Japan

[73] Assignee: Kao Corporation, Tokyo, Japan

[21] Appl. No.: 925,384

[22] Filed: Oct. 31, 1986

[30] Foreign Application Priority Data

Nov. 27, 1985 [JP] Japan ................................ 60-266486
Aug. 1, 1986 [JP] Japan ................................ 61-181653

[51] Int. Cl.$^4$ .............................................. C07F 9/09
[52] U.S. Cl. ..................................... 558/92; 558/169
[58] Field of Search ................................ 558/169, 92

[56] References Cited

U.S. PATENT DOCUMENTS 3,264,378  8/1966  Dailey et al. ..................... 558/169

Primary Examiner—Anton H. Sutto
Attorney, Agent, or Firm—Oblon, Fisher, Spivak, McClelland & Maier

[57] ABSTRACT

A novel phosphoric ester represented by the following formula (I):

$$R^1OPOCH_2CHCOOM^2 \quad (I)$$

(with $\|O$ above P, and $OM^1$, $NH_2$ below)

is produced by halogenating the hydroxyl group of a monoalkyl phosphoric acid, reacting the halogenated product with N-benzoyloxycarbonyl serine ester and then removing protecting groups for the carboxyl group and amino group.

According to the present production process, the phosphoric ester can be obtained inexpensively at a high yield and high purity. Further, the phosphoric ester has a structure similar to that of the phospholipid and has nitrogen-containing polar groups such as amino group in one molecule, so that it has excellent emulsification ability and moisture keeping function. It is thus useful as emulsifiers, humectants and the like.

3 Claims, 2 Drawing Sheets

δ (ppm)

PHOSPHORIC ESTER AND PROCESS FOR PRODUCING SAME

BACKGROUND OF THE INVENTION

1. Field of the Invention

This invention relates to a novel phosphoric ester and, more specifically, to a phosphoric ester having serine or its salt as a substituent.

2. Description of the Prior Art

Heretofore, as those phosphoric esters having nitrogen-containing polar groups such as amino or ammonium groups in the molecule, phospholipids typically represented by natural phosphatidyl choline, phosphatidyl ethanolamine, phosphatidyl serine and sphingolipid have been well-known. Since these phospholipids contain both hydrophobic and hydrophilic groups in one molecule and show interfacial activity such as surface activity and emulsification activity, they are used in various fields.

Further, it has been known that these phospholipids exist in a large amount in the cells of living bodies and are a main component of bio-membranes. It has been gradually made clear in recent years that these lipids not only exist as the constituents for the bio-membranes in the living body but provide various important physiological effects in the living body. For instance, it has been elucidated that the platelet activating factor (PAF) which is one of ether type phospholipids having a structure similar to that of phosphatidyl choline exhibits antihypertensive, hemolizing and immunologically active effects in an extremely small amount. It has also gradually been made clear that the phosphatidyl serine contributes to various life activities by activating, under the coexistence of diglyceride and calcium ions in the living body, the protein kinase C which is a phosphorylating enzyme independent of adenosine triphosphate (ATP). Furthermore, it has also been disclosed that lysophosphatidyl serine obtained by hydrolyzing the acyl group on the 2-position of phosphatidyl serine is involved with allergy reactions or the like.

Accordingly, it has also been expected that those materials similar in structure to the phospholipids having the above described bioactivities, that is, those phosphoric esters having nitrogen-containing polar groups such as amino or ammonium groups in one molecule have various activities and functions. Development of phosphoric esters has been desired which are homologues of phospholipids having nitrogen-containing polar groups such as amino groups and are capable of being synthesized in high purity in a simple procedure using inexpensive and easily available starting materials.

However, since the synthesis of phospholipids is generally very difficult and requires in most cases multi-stages of reactions, the aimed compounds can be obtained only in low yield (for instance refer to E. Baer, et al in Journal of the American Chemical Society, 72, 942 (1950) and "Lipids" edited by Tamio Yamakawa, published from Kyoritsu Shuppan (1973)).

Further, some studies have been reported for the synthesis of phosphoric esters having the structure similar to the phospholipids. However, they require multistages of reactions and starting materials difficult to be synthesized, separation of the aimed product after the reaction is often difficult, the yield is low and the performances of the thus obtained compounds are often insufficient (for example, refer to Japanese patent publication Nos. 23330/1967 and 1654/1973, U.S. Pat. No. 3,507,937).

SUMMARY OF THE INVENTION

In view of such situation, the present inventors have made an earnest study and, as a result, have found a phosphoric ester similar to phosphatidyl serine, i.e., phospholipid containing serine as one of amino acids which is capable of being synthesized in a simple procedure and at high purity using inexpensive and easily available starting materials, as well as a process for producing the same, and thus accomplished this invention.

That is, this invention provides a phosphoric ester represented by the general formula (I):

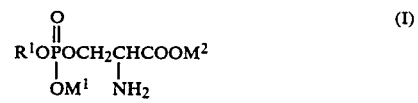

wherein $R^1$ represents:
$R^2$ represented by the following formula (II):

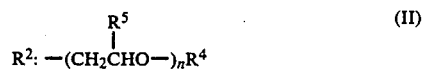

in which $R^4$ represents a linear or branched alkyl group having 8 to 36 carbon atoms in which one or more hydrogen atoms may be substituted with fluorine atoms, $R^5$ represents a hydrogen atom, methyl or ethyl group and n is a number from 0 to 20; or
$R^3$ represented by the following formula (III):

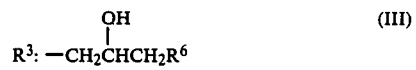

in which $R^6$ is represented by $R^7$ or $OR^8$ wherein $R^7$ and $R^8$ individually represent a linear or branched alkyl group having 8 to 36 carbon atoms and hydrogen atoms therein may be substituted with fluorine atoms, $M^1$ and $M^2$ which may be identical or different with each other individually represent a hydrogen atom, alkali metal, alkanol amine or ammonium. Further, this invention provides a novel process for producing the phosphoric ester represented by the formula (I) as described above.

DETAILED DESCRIPTION OF THE INVENTION AND PREFERRED EMBODIMENTS

Figure 1:
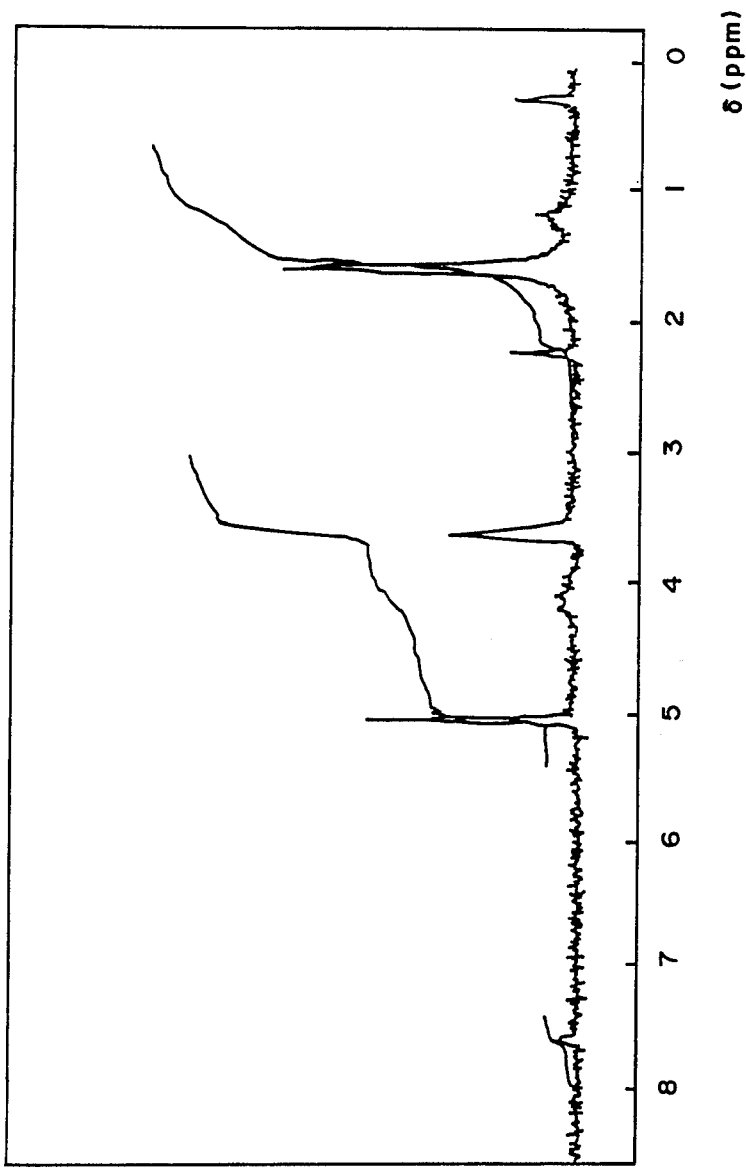
FIG. 1 is a chart illustrating $^1$H-NMR spectrum of 2-amino-2-carboxyethyl-lauryl phosphoric acid obtained in Example 1.

In the phosphoric ester according to this invention, the linear or branched alkyl group having 8 to 36 carbon atoms represented by $R^4$ can include, for example, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, 2-ethylhexyl, 2-butyloctyl, 2-hexyldecyl, 2-hexyldodecyl, 2-ethylhexadecyl, 2-octyldodecyl, 2-butylhexadecyl, 2-octyltetradecyl, 2-hexylhexadecyl, 2-butyloctadecyl, 2-ethyleicosyl, 2-decyltetradecyl, 2-decylhexadecyl, 2-hexyleicosyl, 2-ethyltetraeicosyl, 2-dodecylhexadecyl, 2-tetradecyloctadecyl or 2-hexadecyleicosyl, tridecafluorooctyl, heptadecafluorodecyl, heneicosafluorododecyl, pentacosafluorotetradecyl, nonacosafluohexadecyl, tritriacontafluooctadecyl, 2-pentafluoroethylpentafluorohexyl, 2-tridecafluorohexyltrideca-fluorodecyl, 2-heptadecafluorooctylheptadecafluorododecyl, 2-heneicosafluorodecylheneicosafluorotetradecyl, 2-pentacosafluorododecylpentacosafluorohexadecyl, 2-nonacosafluorotetradecylnonacosafluorooctadecyl. $R^5$ represents a hydrogen atom, methyl or ethyl group. $R^6$ in the formula (III) is represented by $R^7$ or $OR^8$, and $R^7$ and $R^8$ can include the same substituents as those for $R^4$ in the formula (II). Alkali metal in $M^1$ and $M^2$ can include sodium and potassium, and the alkanol amine can include triethanolamine and the like.

The phosphoric ester represented by the formula (I) in this invention may be produced in accordance with the following reaction scheme:

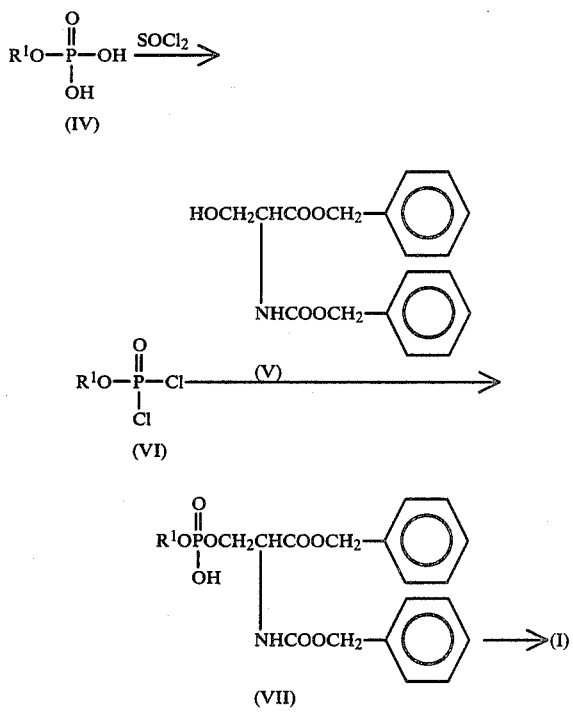

in which $R^1$ has the same meaning as above.

That is, a dihalophosphoridate as shown by the formula (VI) can be obtained by reacting a halogenating reagent such as thionyl chloride with the monoalkyl phosphoric acid of the formula (IV), in which the amount of halogenating agent to be used is such that from 2 to 10 mol of halogen can be produced per one mol of the monoalkyl phosphoric acid. The reaction may be carried out either in the presence of an inert solvent of an ether type such as tetrahydrofuran, hydrocarbon type such as normal hexane, or halogen type such as chloroform and carbon tetrachloride, or in the absence of the solvent, and at 0°–100° C., preferably, from 40° to 80° C.

Then, N-benzyloxycarbonyl serine ester shown by the formula (V) is reacted with dihalophosphoridate of the formula (IV) at a molar ratio of from 1 to 5 mol, preferably, from 1 to 2 mol of N-benzyloxycarbonyl serine ester per one mol of dihalophosphoridate, in an inert solvent such as chloroform or in the absence of the solvent and in the presence of an amine, for example, pyridine or quinoline at 0°–100° C. and, preferably, 0°–50° C. Upon completion of the reaction hydrolysis is conducted by adding water to the reaction system in excess equivalence of halogenated dihalophosphoridate, to obtain the phosphoric ester represented by the formula (VII). Finally, the phosphoric ester shown by the formula (I) can be obtained by heating the thus obtained phosphoric ester shown by the formula (VII) at a methanol reflux temperature, for example, in acetic acid/methanol in the presence of hydrogenation metal catalyst such as palladium to effect debenzylation.

These compounds can be purified by separating to remove impurities by means of silica gel column chromatography or the like.

As has been described above, since the phosphoric ester according to this invention has a structure similar to that of the phospholipid and has nitrogen-containing polar groups such as amino group in one molecule, it has excellent emulsification ability and moisture keeping function. It is thus useful as novel emulsifiers, humectants and the like.

Further, the phosphoric ester having such excellent properties can be obtained at a reduced cost and in a high yield by the production process according to this invention.

This invention will now be described referring to examples. This invention is no way limited to the following examples.

EXAMPLE 1

100.0 g (0.38 mol) of monolauryl phosphoric acid and 134.4 g (1.13 mol) of thionyl chloride were charged in a reactor and heated under stirring at 50° C. for 4 hours under a nitrogen gas stream. After the reaction was completed, 100 ml of chloroform was added to dissolve the reaction product and 103.4 g (0.80 mol) quinoline was added and stirred. The solution was added dropwise at 0° C. under a nitrogen gas stream to a solution prepared by dissolving 157.5 g (0.46 mol) of benzyl-N-benzyloxycarbonyl serine into 100 ml of chloroform and cooled to 0° C. Stirring was effected at 0° C. for 4 hours and then the reaction temperature was raised to room temperature, at which temperature stirring was effected for another 4 hours. After the reaction was completed, the reactant was added with 100 ml of water and stirred at 20° C. for one hour. Then, the solvent was distilled off and the residue was extracted from diethyl ether. After washing the thus obtained ether layer with an aqueous solution of hydrochloric acid, ether was distilled off. The thus obtained residue was dissolved in methanol and reacted with hydrogen blown to the reactor under heating at reflux temperature of methanol at a normal pressure and in the presence of palladium/carbon catalyst for about 10 hours. Then, methanol was distilled off and the resultant residue was purified on silica gel column chromatography (eluent/chloroform:methanol=90:10). When 63.5 g of the thus obtained white solids were analyzed, the following results were obtained to prove that the compound is 2-amino-2-carboxyethyl-lauryl phosphoric acid (0.18 mol, yield 47.3%).

Figure 2:
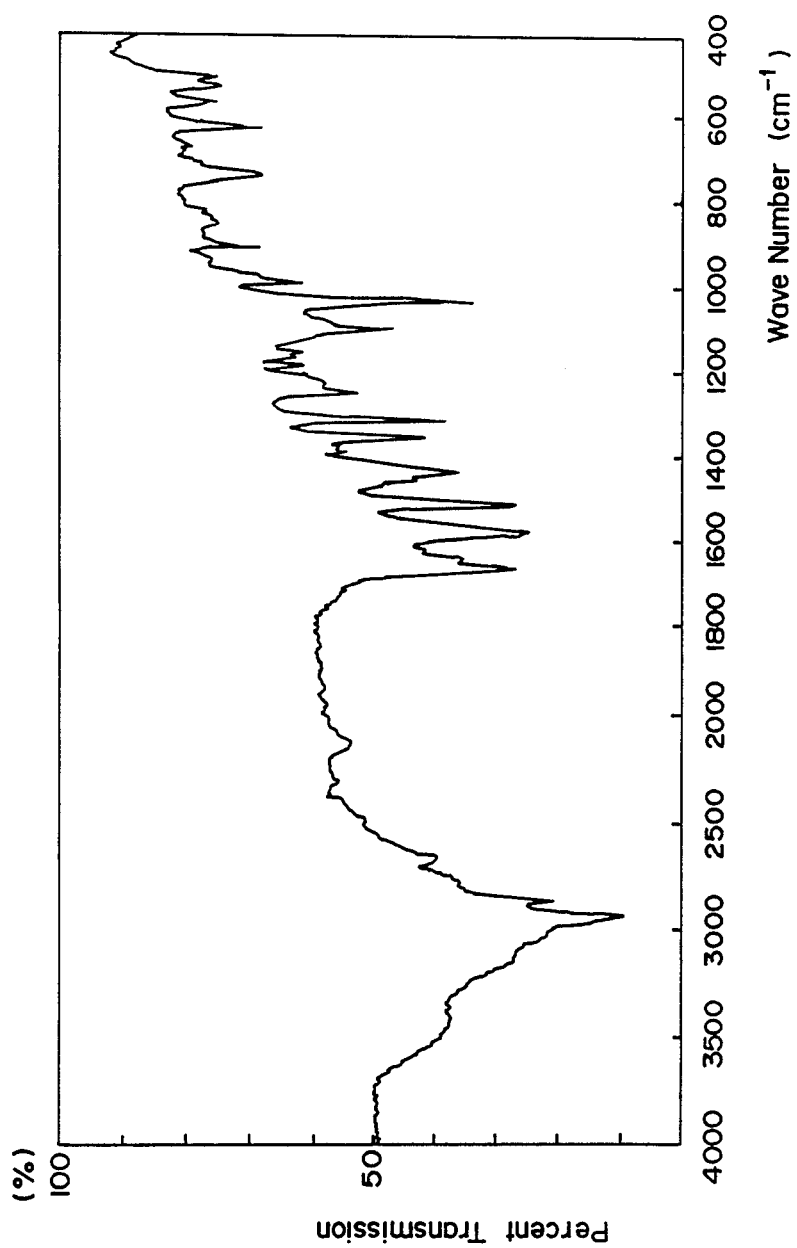
FIG. 2 is a chart illustrating IR spectrum of the same compound.

When the phosphoric ester was analyzed, the following results were obtained and the ester was proved to be an aimed phosphoric ester.
Elementary analysis (% by weight)
Calculated: C: 50.99, H: 9.13, N: 3.96, P: 8.76
Found: C: 50.78, H: 9.02, N: 3.88, P: 8.76
$^1$H-NMR (solvent: CDCl$_3$/CD$_3$OD): FIG. 1
δ: 0.87 (broad, s, 3H)
1.27 (broad, s, 21H)
3.30 (m, 4H+MeOH)
3.60- 3.96 (m, 1H)
IR (KBr): FIG. 2
3420, 2940, 1670, 1580, 1520, 1420, 1030, 990 (cm$^{-1}$)

EXAMPLE 2

100.0 g (0.29 mol) of monooctadecyl phosphoric acid and 103.5 g (0.87 mol) of thionyl chloride were charged in a reactor and brought into reaction in the same manner as in Example 1. After the reaction was completed, a solution prepared by adding 51.4 g (0.65 mol) of pyridine and dissolving in the same procedure as in Example 1 was added dropwise in the same manner as in Example 1 to a solution prepared by dissolving 120.2 g (0.35 mol) of benzyl-N-benzyloxycarbonyl serine and, thereafter, 67.3 g of 2-amino-2-carboxyethyl-octadecyl phosphoric acid was obtained as a white solid in the procedure as in Example 1 (0.15 mol, yield 53.0%).
Elementary analysis (wt %)
Calculated: C: 57.64, H: 10.14, N: 3.20, P: 7.08
Found: C: 57.60, H: 10.19, N: 3.07, P: 6.99

EXAMPLE 3

100.0 g (0.26 mol) of mono(2-octyldodecyl) phosphoric acid and 79.8 g (0.67 mol) of thionyl chloride were reacted in the same procedure as in Example 1 to obtain dichlorophosphoridate. A solution prepared by mixing the reaction product with 84.0 g (0.65 mol) of quinoline was added dropwise at 0° C. to chloroform in which 107.8 g (0.31 mol) of benzyl-N-benzyloxycarbonyl serine were dissolved and, thereafter, 58.8 g of aimed 2-amino-2-carboxyethyl-2-octyldodecyl phosphoric acid were obtained as a white solid in the same procedure as in Example 1 (0.12 mol, yield 48.6%).
Elementary analysis (wt %)
Calculated: C: 59.33, H: 10.39, N: 3.01, P: 6.65
Found: C: 59.27, H: 10.39, N: 2.96, P: 6.43

EXAMPLE 4

Dichlorophosphoridate was obtained from 100.0 g (0.26 mol) of mono(2-ethyltetraeicosyl) phosphoric acid and 99.5 g (0.84 mol) of thionyl chloride in the same procedure as in Example 1. Then, 72.5 g (0.60 mol) of quinoline and 120.9 g (0.35 mol) of benzyl-N-benzyloxycarbonyl serine were used to obtain 87.5 g of aimed 2-amino-2-carboxyethyl-2-ethyltetraeicosyl phosphoric acid as a white solid (0.16 mol, yield 61.2%).
The result of the elementary analysis was as follows.
Elementary analysis (wt %)
Calculated: C: 63.36, H: 11.00, N: 2.55, P: 5.63
Found: C: 63.26, H: 10.89, N: 2.53, P: 5.52

EXAMPLE 5

Dichlorophosphoridate was obtained by using 100.0 g (0.29 mol) of mono(2-hydroxy-3-lauryloxypropyl) phosphoric acid and 105.0 g (0.88 mol) of thionyl chloride. Then, 55.4 g (0.70 mol) of pyridine and 179.6 g (0.52 mol) of benzyl-N-benzylcarbonyl serine were dissolved in 100 ml of chloroform and stirred at 0° C. for 4 hours. Then, the reaction temperature was raised to room temperature and agitation was effected for 4 hours. After the reaction was completed, 100 ml of water were added and stirred at 20° C. for one hour. Then, the solvent was distilled off and the residue was extracted from ethylether. The thus obtained residue was dissolved in methanol and hydrogen was blown while refluxing methanol by heating to effect hydrogenation reaction for about 10 hours at a normal pressure by using a palladium/carbon catalyst at a normal pressure. After the reaction was completed, the residue obtained by distilling off methanol was purified on silica gel column chromatography (eluent/chloroform:methanol=90:10), to obtain 39.7 g of aimed 2-amino-2-carboxyethyl-(2-hydroxy-3-lauryloxypropyl) phosphoric acid as a white solid (0.09 mol, yield 32.0%).
The result of the elementary analysis was as shown below.
Elementary analysis (wt %)
Calculated: C: 50.58, H: 8.99, N: 3.28, P: 7.24
Found: C: 50.55, H: 8.92, N: 3.25, P: 7.18

EXAMPLE 6

Dichlorophosphoridate was obtained from 100.0 g (0.25 mol) of monotetraoxyethylene monolauryl ether phosphoric acid and 90.5 g (0.76 mol) of thionyl chloride. Then, 103.6 g (0.30 mol) of benzyl-N-benzyloxycarbonyl serine and 90.4 g (0.70 mol) of quinoline were used and same procedure as in Example 1 were applied to obtain 43.6 g of 2-amino-2-carboxyethyltetraoxyethylene monolauryl ether phosphoric acid as a white solid (0.08 mol, yield 32.9%).
The result of the elementary analysis was as shown below.
Elementary analysis (wt %)
Calculated: C: 52.16, H: 9.14, N: 2.64, P: 5.85
Found: C: 52.01, H: 9.13, N: 2.61, P: 5.73

EXAMPLE 7

Dichlorophosphoridate was obtained from 100.0 g (0.094 mol) of octadecyloxyethylene monolauryl ether phosphoric acid and 33.7 g (0.28 mol) of thionyl chloride. Then, 46.6 g (0.14 mol) of benzyl-N-benzyloxycarbonyl serine and 22.4 g (0.28 mol) of pyridine were used and the same procedure as in Example 1 was applied to obtain 17.3 g of 2-amino-2-carboxyethyloctadecyloxyethylene monolauryl ether phosphoric acid as a white solid (0.015 mol, yield 16.0%).
The result of the elementary analysis was as shown below.
Elementary analysis (wt %)
Calculated: C: 53.44, H: 9.14, N: 1.22, P: 2.70
Found: C: 53.28, H: 9.02, N: 1.19, P: 2.73

EXAMPLE 8

Dichlorophosphoridate was obtained from 100.0 g (0.30 mol) of 2-hydroxyhexadecyl phosphoric acid and 105.5 g (0.89 mol) of thionyl chloride. Then, 146.0 g (0.44 mol) of benzyl-N-benzyloxycarbonyl serine and 70.1 g (0.89 mol) of pyridine were used and the same procedure as in Example 1 was applied to obtain 24.6 g of 2-amino-2-carboxyethyl-2-hydroxyhexadecyl phosphoric acid as a white solid (0.058 mol, yield 19.6%).
The result of the elementary analysis was as shown below.
Elementary analysis (wt %)
Calculated: C: 53.63, H: 9.48, N: 3.29, P: 7.28
Found: C: 53.48, H: 9.45, N: 3.35, P: 7.19

EXAMPLE 9

Dichlorophosphoridate was obtained from 100.0 g (0.18 mol) of monoheptadecafluorodecyl phosphoric acid and 64.3 g (0.54 mol) of thionyl chloride. Then, 86.3 g (0.26 mol) of benzyl-N-benzyloxycarbonyl serine and 42.4 g (0.54 mol) of pyridine were used and the same procedure as in Example 1 was applied to obtain 17.6 g of 2-amino-2-carboxyethyl-heptadecafluorodecyl phosphoric acid as a white solid (0.028 mol, yield 15.4%).

The result of the elementary analysis was as shown below.

Elementary analysis (wt %)
Calculated: C: 24.72, H: 1.74, N: 2.22, P: 4.91 F: 51.19
Found: C: 24.65, H: 1.77, N: 2.29, P: 4.95 F: 51.10

TEST EXAMPLE 1

Skin cream having the following formulation was prepared by using mono-sodium 2-amino-2-carboxyethyl lauryl phosphate synthesized in Example 1. It was neutral or weakly acidic cream, which was in a preferable emulsified state with favorable fitting and with no sticking.

| | |
|---|---|
| 2-amino-2-carboxyethyl-lauryl phosphoric acid | 1.2 (wt %) |
| Glycerine monostearate | 2.4 |
| Cetanol | 4.0 |
| Solid paraffin | 5.0 |
| Squalane | 10.0 |
| Octyldodecyl myristate | 6.0 |
| Glycerine | 6.0 |
| Perfume, colorant, antiseptic | appropriate amount |
| Ion exchanged water | balance |

What is claimed is:

1. A process for producing a phosphoric ester represented by the following formula (I):

wherein $R^1$ represents:

$R^2$ represented by the following formula (II):

in which $R^4$ represents a linear or branched alkyl group having 8 to 36 carbon atoms in which one or more hydrogen atoms may be substituted with fluorine atoms, $R^5$ represents a hydrogen atom, methyl or ethyl group and n is a number from 0 to 20; or $R^3$ represented by the following formula (III):

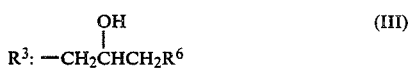

in which $R^6$ represents $R^7$ or $OR^8$ wherein $R^7$ and $R^8$ represent individually a linear or branched alkyl group having 8 to 36 carbon atoms and one or more hydrogen atoms therein may be substituted with fluorine atoms, $M^1$ and $M^2$ which may be identical or different with each other represent individually a hydrogen atom, alkali metal, alkanol amine or ammonium, which comprises halogenating at a temperature of 0°–100° C. in an inert solvent or in the absence of a solvent the hydroxyl group of a monoalkyl phosphoric acid represented by the following formula (IV):

in which $R^1$ has the same meaning as described above, with a halogenating agent in an amount such that from 2–10 moles of halogen can be produced per one mole of the monoalkyl phosphoric acid, reacting the halogenated product with N-benzyloxycarbonyl serine ester represented by the following formula (V):

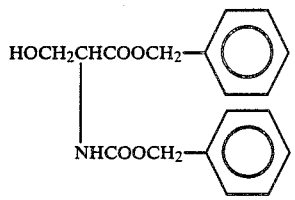

in a molar ratio of from 1–5 moles of N-benzyloxycarbonyl serine ester per one mole of halogenated product in an inert solvent or in the absence of a solvent at 0°–100° C. and then removing protecting groups for the carbonyl group and amino group by hydrogenation in the presence of a hydrogenation metal catalyst.

2. A process according to claim 1, wherein said halogenating agent is thionyl chloride.

3. A phosphoric ester represented by the following formula (I):

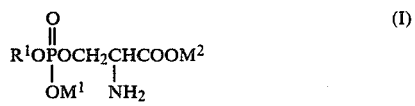

wherein $R^1$ represents:

$R^2$ represented by the following formula (II):

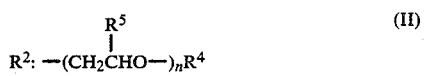

in which $R^4$ represents a linear or branched alkyl group having 8 to 36 carbon atoms in which one or more hydrogen atoms may be substituted with fluorine atoms, $R^5$ represents a hydrogen atom, methyl or ethyl group and n is a number from 0 to 20; or $R^3$ represented by the following formula (III)

$$R^3: -CH_2CHCH_2R^6 \quad \text{(III)}$$
$$\quad\;\;|$$
$$\quad OH$$

in which $R^6$ represents $R^7$ or $OR^8$ wherein $R^7$ and $R^8$ represent individually a linear or branched alkyl group having 8 to 36 carbon atoms and one or more hydrogen atoms therein may be substituted with fluorine atoms, $M^1$ and $M^2$ which may be identical or different with each other represent individually a hydrogen atom, alkali metal, alkanol amine or ammonium.

* * * * *